United States Patent [19]

Eggl

[11] Patent Number: 5,251,778
[45] Date of Patent: Oct. 12, 1993

[54] DISPENSER BOX FOR GRADUATED VESSELS

[75] Inventor: Wilfried Eggl, Lemgo, Fed. Rep. of Germany

[73] Assignee: Heinrich Amelung GmbH, Lemgo, Fed. Rep. of Germany

[21] Appl. No.: 15,558

[22] Filed: Feb. 9, 1993

[30] Foreign Application Priority Data

Feb. 25, 1992 [DE] Fed. Rep. of Germany ....... 9202381

[51] Int. Cl.$^5$ .............................................. B65D 43/04
[52] U.S. Cl. ..................................... 220/526; 220/256; 220/351; 220/23.83; 422/104; 206/438
[58] Field of Search ................. 206/526, 438, 45.31; 422/104, 102; 221/268, 303, 107; 220/256, 523, 526, 351, 346, 345, 23.4, 23.83, 23.86, 403

[56] References Cited

U.S. PATENT DOCUMENTS

| | | | |
|---|---|---|---|
| 3,334,734 | 8/1967 | Meyers | 206/45.31 |
| 3,405,836 | 10/1968 | Regis, Jr. | 220/256 |
| 3,451,536 | 6/1969 | O'Leary et al. | 206/45.31 |
| 3,960,270 | 6/1976 | May | 220/523 |
| 4,444,310 | 4/1984 | Odell | 206/438 |
| 4,572,365 | 2/1986 | Bruno et al. | 206/526 |
| 4,911,298 | 3/1990 | Miyagawa et al. | 206/45.31 |
| 4,966,296 | 10/1990 | Farrell | 220/23.83 |
| 5,060,852 | 10/1991 | Beckerman et al. | 206/45.31 |
| 5,173,741 | 12/1992 | Wakatake | 422/104 |

FOREIGN PATENT DOCUMENTS 469320 2/1992 European Pat. Off. ............ 221/303

*Primary Examiner*—Allan M. Shoap
*Assistant Examiner*—S. Castellano
*Attorney, Agent, or Firm*—Henry M. Feiereisen

[57] ABSTRACT

In a dispenser box for containment of graduated vessels of a type having an inlet opening for receiving fluids to be tested such as blood, blood plasma or the like, with the dispenser box having a longitudinal side provided with an ejection slot and a top side provided with spaced and parallel rectangular openings, wherein the inlet openings of the vessels face the openings in the top side, a sheet is removably secured between the top side of the housing and the vessels and covering the inlet openings of the vessels.

8 Claims, 1 Drawing Sheet

DISPENSER BOX FOR GRADUATED VESSELS

BACKGROUND OF THE INVENTION

The present invention refers to a dispenser box or storage box for containment of graduated vessels of the type having an inlet opening for receiving fluid to be tested such as blood, blood plasma or the like, with the dispenser box having a longitudinal side provided with an ejection slot and a top side formed with spaced and parallel rectangular openings, with the inlet openings of the vessels facing the openings in the top side.

Dispenser boxes of this type are used for automatically supplying graduated vessels to an analyzer. The openings in the top side as well as the ejection slot are engageable by slides of a transport device by which the individual graduated vessels are continuously fed to the analyzer.

In order to eliminate possible contamination of the vessels, e.g. through penetration of dirt through the top side openings into the open vessels, it has been proposed to completely envelope the dispenser box with a protective sheet, once the vessels were placed within the dispenser box. The protective sheet is provided with a tear-off strip for allowing a convenient removal of the sheet before the dispenser box is inserted in the feed unit. This type of protective wrapping is however disadvantageous because a relatively great amount of sheet material for achieving the desired protection is required. In addition, the necessary amount of sheet material poses also a problem with respect to its disposal after being removed from the dispenser box. Taking into account the increased desire for waste prevention, the use of such protective wrappings is problematic, especially when further considering that a great number of graduated vessels is utilized, creating a significant amount of sheet waste.

Generally, the application of these graduated vessels is improved by inserting small steel balls into the vessels to allow an analysis of the fluids not only by means of photometric measurements but also through measurements according to the so-called "ball method" in which spherical bodies are loosely fed into the graduated vessels before placement of the vessels in the dispenser box. By completely enveloping the dispenser box with a protective sheet in a manner proposed by the prior art, there is the possibility of balls falling out of the vessels, thus rendering the vessels unsuitable for use in an automatic analyzing process.

SUMMARY OF THE INVENTION

It is thus an object of the present invention to provide an improved dispenser box obviating the afore-stated drawbacks.

In particular, it is an object of the present invention to provide an improved dispenser box which considerably improves the secure containment of graduated vessels, without generating excessive waste.

These objects and others which will become apparent hereinafter, are attained in accordance with the present invention by arranging a sheet upon the vessels to cover the inlet opening of the vessels, and removably securing the sheet between the top side of the dispenser box and the vessels, when the vessels are placed in the dispenser box.

By sandwiching the sheet between the top side of the dispenser box and the vessels, the size of the sheet can be reduced to the dimension of the top side, i.e. in correspondence with a broadside of the dispenser box, resulting in only a fraction of sheet material being used compared to the enveloping sheet as proposed by the prior art. In this manner the overall costs are reduced while significantly improving the problem of disposal.

The sheet is securely clamped between the top side of the dispenser box and the vessels and thus is prevented from any shifting. Since the sheet is directly placed upon the vessels and seals off the inlet openings, the spherical bodies contained in the vessels are prevented from falling out even when the dispenser box is held upside down and the inlet openings of the vessels face downwards, e.g. during transport.

Preferably, the sheet is provided with a central tab which projects into the ejection slot for allowing easy removal of the sheet through pulling the tab.

A further advantage of the present invention is the protection of the sheet itself by the top side of the dispenser box so that the possibility of damage to the sheet and any danger of contamination of the graduated vessels is significantly reduced.

BRIEF DESCRIPTION OF THE DRAWING

The above and other objects, features and advantages of the present invention will now be described in more detail with reference to the accompanying drawing in which the sole FIGURE shows a perspective illustration of one embodiment of a dispenser box according to the present invention.

DETAILED DESCRIPTION OF A PREFERRED EMBODIMENT

Figure 1:
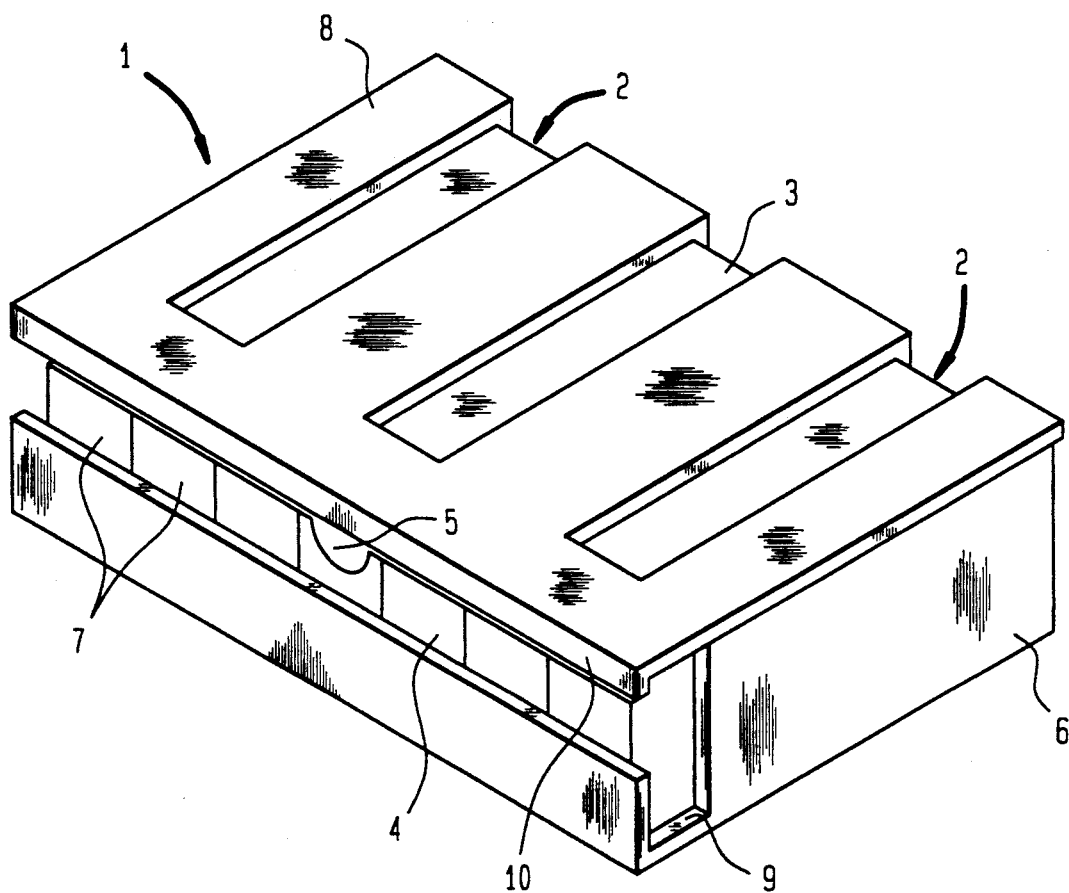

The sole FIGURE shows a perspective view of one embodiment of a dispenser box or storage box according to the present invention, generally designated by reference numeral 1. The dispenser box 1 includes a housing 6 of generally rectangular cross section for containment of a plurality of block-shaped graduated vessels for receiving fluids to be tested, such as blood, blood plasma, or the like, with the vessels 7 being arranged in side-by-side relationship within the housing 6.

The housing 6 of the dispenser box 1 has a broadside-defining top side 8 which includes three elongated or rectangular openings 2 extending parallel at a distance to each other transversal to the longitudinal axis of the housing 6. These openings 2 are engageable by a (not shown) slider or similar device of a feed unit by which the graduated vessels 7 are transported to an analyzer. Extending along the front longitudinal side of the housing 6 is an ejection slot 4 which at each axial end face of the housing 6 is in communication with a discharge opening 9 is of sufficient dimension to allow vessels 7 to be ejected therethrough.

Each block-shaped vessel 7 faces with its inlet opening (not shown) the top side 8 of the housing 6. Sandwiched between the top side 8 and the vessels 7 is a sheet or foil 3 which covers the inlet opening of the vessels 7 and extends essentially over the entire area formed by the top side 8. As shown in the FIGURE, in the area of the ejection slot 4, the top side 8 is bent at right angle to define an edge 10, with the sheet 3 thus being wrapped around the inlet openings of the vessels 7 in proximity of the ejection slot 4 and clamped between the angled edge 10 and the vessels 7. In this area, the sheet 3 is provided at a central location thereof with a tab 5 which projects into the ejection slot 4 and allows withdrawal of the sheet 3 from the dispenser box 1.

The sheet 3 is loosely placed upon the vessels 7 before being inserted in the housing 6 of the dispenser box 1. Thus, no adhesive particles can enter the vessel 7, and the sheet 3 is made of a material from which no particles, such as lint, can be released. A suitable material for use as a sheet 3 includes thermoplastics such as polyethylene, polystyrene, or metals such as aluminum or copper. After being covered by the sheet 3, the vessels 7 are inserted in the dispenser box 1 until the front row of vessels 7 bears upon the front longitudinal side along the ejection slot 4, with the sheet 3 being wrapped around the inlet openings of the vessels 7 by the angled edge 10 and securely clamped between the vessels 7 and the top side 8.

While the invention has been illustrated and described as embodied in a dispenser box for containment of graduated vessels, it is not intended to be limited to the details shown since various modifications and structural changes may be made without departing in any way from the spirit of the present invention.

What is claimed as new and desired to be protected by Letters Patent is set forth in the appended claims:

I claim:

1. In a dispenser box for containment of graduated vessels of a type having an inlet opening for receiving fluids to be tested, the dispenser box having a broadside-defining top side provided with spaced and parallel elongated openings, with the inlet openings of the vessels facing the openings in the top side, and a longitudinal side provided with an ejection slot, the improvement comprising a sheet removably secured between the top side of the dispenser box and the vessels and covering the inlet openings of the vessels.

2. The dispenser box defined in claim 1 wherein the top side is bent in direction of the ejection slot to define an angled edge, said sheet being clamped between the angled edge and the vessels.

3. The dispenser box defined in claim 1 wherein the sheet is provided with a tab projecting into the ejection slot.

4. The dispenser box defined in claim 1 wherein the tab is situated at a central location of the sheet.

5. The dispenser box defined in claim 1 wherein the dispenser box is of rectangular configuration.

6. The dispenser box defined in claim 1 wherein the top side openings are of rectangular configuration.

7. The dispenser box defined in claim 1 wherein the sheet is of a size essentially corresponding to the dimension of the top side.

8. In combination, a dispenser box adapted for containment of vessels of a type having an inlet opening for receiving fluids for testing, the dispenser box having a top side provided with spaced and parallel openings, with the inlet openings of the vessels facing the openings of the top side, and a longitudinal side provided with an ejection slot, and a sheet removably secured between the top side of the dispenser box and the vessels and covering the inlet openings of the vessels.

* * * * *